US006401519B1

(12) United States Patent
McFarland et al.

(10) Patent No.: US 6,401,519 B1
(45) Date of Patent: *Jun. 11, 2002

(54) SYSTEMS AND METHODS FOR CHARACTERIZATION OF MATERIALS AND COMBINATORIAL LIBRARIES WITH MECHANICAL OSCILLATORS

(75) Inventors: Eric W. McFarland, San Jose; Leonid Matsiev, Cupertino, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/723,818

(22) Filed: Nov. 28, 2000

Related U.S. Application Data

(60) Division of application No. 08/946,921, filed on Oct. 8, 1997, now Pat. No. 6,182,499, which is a continuation-in-part of application No. 08/898,715, filed on Jul. 22, 1997, now Pat. No. 6,030,917.

(60) Provisional application No. 60/050,949, filed on Jun. 13, 1997, provisional application No. 60/048,987, filed on Jun. 9, 1997, provisional application No. 60/035,366, filed on Jan. 10, 1997, provisional application No. 60/035,202, filed on Jan. 10, 1997, provisional application No. 60/029,255, filed on Oct. 25, 1996, provisional application No. 60/028,106, filed on Oct. 9, 1996, and provisional application No. 60/028,105, filed on Oct. 9, 1996.

(51) Int. Cl.[7] .............................................. G01N 29/02
(52) U.S. Cl. .................... 73/24.6; 73/31.06; 73/30.04; 73/32 A; 73/54.24; 73/54.38; 73/54.41; 73/61.49; 73/61.75; 73/61.79; 422/68.1
(58) Field of Search .................... 73/24.01, 24.03, 73/24.04, 24.05, 24.06, 30.01, 30.04, 31.01, 31.02, 31.03, 31.05, 31.06, 32 A, 32 R, 53.01, 54.01, 54.02, 54.23, 54.24, 54.25, 54.26, 54.38, 54.41, 61.45, 61.49, 61.75, 61.79, 579; 310/360, 316, 320; 422/68.1, 75, 98

(56) References Cited

U.S. PATENT DOCUMENTS

| 3,622,968 | A | 11/1971 | Silverman |
| 3,718,032 | A | 2/1973 | Gray |
| 3,778,757 | A | 12/1973 | Houston |

(List continued on next page.)

FOREIGN PATENT DOCUMENTS

| EP | 0102490 | 3/1984 |
| EP | 02822511 | 9/1988 |
| EP | 0676638 | 10/1995 |

OTHER PUBLICATIONS

J. Hlavay, et al.; "Applications of the Piezoelectric Crystal Detector in Analytical Chemistry," *Analytical Chemistry*, vol. 49, No. 13 (Nov. 1977), pp. 1890–1898.

H. Muramatsu, et al.; "Computation of Equivalent Circuit Parameters of Quartz Crystals in Contact with Liquids and Study of Liquid Properties," *Anal. Chem.*, vol. 60 (1988), pp. 2142–2146.

K. Kanazawa, et al.; "The Oscillation Frequency of a Quartz Resonator in Contact with a Liquid," *Analytica Chimica Acta.*, 175 (1985), pp. 99–105.

*Primary Examiner*—Hezron Williams
*Assistant Examiner*—Rose M. Miller
(74) *Attorney, Agent, or Firm*—Dobrusin & Thennisch PC

(57) ABSTRACT

Methods and apparatus for screening diverse arrays of materials are provided. In one aspect, systems and methods are provided for imaging a library of materials using ultrasonic imaging techniques. In another aspect, systems and methods are provided for generating acoustic waves in a tank filled with a coupling liquid to form a disturbance that is representative of a library of materials. In another aspect of the invention, a mechanical resonator is used to evaluate various properties (e.g., molecular weight, viscosity, specific weight, elasticity, dielectric constant, conductivity, etc.) of the individual liquid elements of a library of materials.

54 Claims, 5 Drawing Sheets

U.S. PATENT DOCUMENTS

| | | | |
|---|---|---|---|
| 3,902,365 A | | 9/1975 | Knauth |
| 4,342,936 A | * | 8/1982 | Marcus et al. ............... 310/330 |
| 4,349,881 A | | 9/1982 | November et al. ......... 73/32 A |
| 4,370,662 A | | 1/1983 | Hou et al. |
| 4,391,338 A | | 7/1983 | Patashnick et al. ............ 73/28 |
| 4,526,480 A | | 7/1985 | Ward |
| 4,543,829 A | | 10/1985 | Lerch |
| 4,596,697 A | | 6/1986 | Ballato |
| 4,721,874 A | | 1/1988 | Emmert |
| 4,729,237 A | | 3/1988 | Suzuki et al. |
| 4,734,609 A | | 3/1988 | Jasime |
| 4,741,200 A | | 5/1988 | Hammerle |
| 4,760,351 A | | 7/1988 | Newell et al. |
| 4,767,719 A | | 8/1988 | Finlan |
| 4,779,451 A | | 10/1988 | Ezawa et al. |
| 4,812,698 A | * | 3/1989 | Chida et al. ................ 310/330 |
| 4,910,523 A | | 3/1990 | Huguenin et al. |
| 4,922,745 A | | 5/1990 | Rudkin et al. |
| 5,179,028 A | | 1/1993 | Vali et al. |
| 5,191,791 A | | 3/1993 | Gerardi et al. |
| 5,201,215 A | * | 4/1993 | Granstaff et al. .......... 73/54.41 |
| 5,224,174 A | | 6/1993 | Schneider et al. |
| 5,253,530 A | | 10/1993 | Letcher, III |
| 5,283,037 A | | 2/1994 | Baer et al. |
| 5,296,374 A | | 3/1994 | Culshaw et al. |
| 5,306,644 A | | 4/1994 | Myerholtz et al. |
| 5,357,964 A | | 10/1994 | Spivey et al. |
| 5,375,470 A | | 12/1994 | Matsushima et al. |
| 5,454,045 A | | 9/1995 | Perkins et al. |
| 5,455,475 A | | 10/1995 | Josse et al. |
| 5,469,369 A | | 11/1995 | Rose-Pehrsson et al. |
| 5,488,866 A | | 2/1996 | Ravel et al. |
| 5,524,636 A | | 6/1996 | Sarvazyan et al. |
| 5,571,401 A | | 11/1996 | Lewis et al. |
| 5,653,939 A | | 8/1997 | Hollis et al. |
| 5,698,089 A | | 12/1997 | Lewis et al. |
| 5,705,399 A | | 1/1998 | Larue |
| 5,734,098 A | * | 3/1998 | Kraus et al. ............... 73/61.62 |
| 5,744,902 A | | 4/1998 | Vig |
| 5,770,038 A | | 6/1998 | Iwama et al. |
| 5,776,359 A | | 7/1998 | Schultz et al. |
| 5,798,452 A | | 8/1998 | Martin et al. |
| 5,852,229 A | * | 12/1998 | Josse et al. ................ 73/24.06 |
| 5,889,351 A | * | 3/1999 | Okumura et al. ........... 310/321 |
| 5,985,356 A | | 11/1999 | Schultz et al. |
| 6,044,694 A | * | 4/2000 | Anderson et al. .......... 73/54.41 |
| 6,182,499 B1 | * | 2/2001 | McFarland et al. ........ 73/24.06 |

OTHER PUBLICATIONS

T. Nomura, et al.; "Electrolytic Determination of Namomolar Concentrations of Silver in Solution with a Piezoelectric Quartz Crystal", *Analytica Chimica Acta.*, 131 (1981), pp. 97–102.

M. R. Fisch et al.; "Improved Acoustic Viscosimeter Technique," *J. Acoust. Soc. Am.*, vol. 60, No. 3 (Sep. 1976), pp. 623–625.

H. Muramatsu, et al.; "A Quartz Crystal Viscosity Sensor for Monitoring Coagulation Reaction and Its Application to a Multichannel Coagulation Detector," *Biosensors & Boielectronics*, vol. 6 (1991), pp. 353–358.

Kipling, Arlin L and Michael Thompson, "Network Analysis Method Applied to Liquid–Phase Acoustic Wave Sensors", Anal. Chem., 1990, pp. 1514–1519, 62.

Michels, A. et al., "1 MHz Quartz Length Extension Resonator as a Probe for Scanning Near–Field Acoustic Microscopy", Thin Solid Films, 1995, pp. 172–175, 264.

PCT International Search Report, dated Apr. 27, 1998.

* cited by examiner

SYSTEMS AND METHODS FOR CHARACTERIZATION OF MATERIALS AND COMBINATORIAL LIBRARIES WITH MECHANICAL OSCILLATORS

CROSS REFERENCE TO RELATED APPLICATIONS

This application is a divisional of commonly assigned U.S. application Ser. No. 08/946,921, now U.S. Pat. No. 6,182,499 B1, filed Oct. 8, 1997, which is a continuation-in-part of commonly assigned U.S. application Ser. No. 08/898,715, now U.S. Pat. No. 6,030,917, filed Jul. 22, 1997, and which claims the benefit of U.S. Provisional Application Nos. 60/050,949, filed Jun. 13, 1997, 60/048,987, filed Jun. 9, 1997, 60/035,366, filed Jan. 10, 1997, 60/035,202, filed Jan. 10, 1997, 60/029,255, filed Oct. 25, 1996, 60/028,106, filed Oct. 9, 1996, and 60/028,105, filed Oct. 9, 1996, the complete disclosures of which are herein incorporated by reference for all purposes.

This application is also related to commonly assigned, U.S. patent applications Ser. No. 08/327,513, now U.S. Pat. No. 5,985,356, filed Oct. 18, 1994, U.S. patent applications Ser. No. 08/438,043, now U.S. Pat. No. 5,776,359, filed May 8, 1995, and U.S. patent applications Ser. No. 08/841,423, now U.S. Pat. No. 6,045,671, filed Apr. 22, 1997; commonly assigned U.S. Provisional Application Serial No. 60/016,102, filed Jul. 23, 1996; and PCT Application No. WO 95/13278, filed Oct. 18, 1995; the complete disclosures of which are incorporated herein by reference for all purposes.

FIELD OF THE INVENTION

The present invention generally relates to methods and apparatus for rapidly screening an array of diverse materials that have been created at known locations on a single substrate surface. More specifically, the invention is directed to the use of ultrasonic and/or mechanical transducers to image and/or evaluate the individual elements of a library of materials.

BACKGROUND OF THE INVENTION

The discovery of new materials with novel chemical and physical properties often leads to the development of new and useful technologies. Currently, there is a tremendous amount of activity in the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and reaction pathways for the synthesis of such solid state compounds.

The preparation of new materials with novel chemical and physical properties is at best happenstance with our current level of understanding. Consequently, the discovery of new materials depends largely on the ability to synthesize and analyze new compounds. Given approximately 100 elements in the periodic table that can be used to make compositions consisting of two or more elements, an incredibly large number of possible new compounds remains largely unexplored. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those collections for molecules having a desired property. An example of such a process is the humoral immune system which in a matter of weeks sorts through some $10^{12}$ antibody molecules to find one which specifically binds a foreign pathogen (Nisonoff et al., *The Antibody Molecule* (Academic Press, New York, 1975)). This notion of generating and screening large libraries of molecules has recently been applied to the drug discovery process.

Applying this logic, methods have been developed for the synthesis and screening of large libraries (up to $10^{14}$ molecules) of peptides, oligonucleotides and other small molecules. Geysen et al., for example, have developed a method wherein peptide syntheses are carried out in parallel on several rods or pins (*J. Immun. Meth.* 102:259–274 (1987), incorporated herein by reference for all purposes). Generally, the Geysen et al. method involves functionalizing the termini of polymeric rods and sequentially immersing the termini in solutions of individual amino acids. In addition to the Geysen et al. method, techniques have recently been introduced for synthesizing large arrays of different peptides and other polymers on solid surfaces. Pirrung et al. have developed a technique for generating arrays of peptides and other molecules using, for example, light-directed, spatially-addressable synthesis techniques (U.S. Pat. No. 5,143,854 and PCT Publication No. WO 90/15070, incorporated herein by reference for all purposes). In addition, Fodor et al. have developed a method of gathering fluorescence intensity data, various photosensitive protecting groups, masking techniques, and automated techniques for performing light-directed, spatially-addressable synthesis techniques (Fodor et al., PCT Publication No. WO 92/10092, the teachings of which are incorporated herein by reference for all purposes).

Using these various methods, arrays containing thousands or millions of different elements can be formed (U.S. patent application Ser. No. 08/805,727, filed Dec. 6, 1991, the complete disclosure of which is incorporated herein by reference for all purposes). As a result of their relationship to semiconductor fabrication techniques, these methods have come to be referred to as "Very Large Scale Immobilized Polymer Synthesis," or "VLSIPS™" technology. Such techniques have met with substantial success in screening various ligands such as peptides and oligonucleotides to determine their relative binding affinity to a receptor such as an antibody.

The solid phase synthesis techniques currently being used to prepare such libraries involve the sequential coupling of building blocks to form the compounds of interest. For example, in the Pirrung et al method polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequence are synthesized. These solid phase synthesis techniques cannot readily be used to prepare many inorganic and organic compounds.

In PCT WO 96/11878, the complete disclosure of which is incorporated herein by reference, methods and apparatus are disclosed for preparing a substrate with an array of diverse materials deposited in predefined regions. Some of the methods of deposition disclosed in PCT WO 96/11878 include sputtering, ablation, evaporation, and liquid dispensing systems. Using the disclosed methodology, many classes of materials can be generated combinatorially including inorganics, intermetallics, metal alloys, and ceramics In general, combinatorial chemistry refers to the approach of creating vast numbers of compounds by reacting a set of starting chemicals in all possible combinations. Since its introduction into the pharmaceutical industry in the late 80's, it has dramatically sped up the drug discovery process and is now becoming a standard practice in the industry (*Chem. Eng. News* Feb. 12, 1996). More recently, combinatorial techniques have been successfully applied to the synthesis of inorganic materials (G. Briceno et al., *SCIENCE* 270, 273–275, 1995 and X. D. Xiang et al., *SCIENCE* 268, 1738–1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors. Discovery of heterogeneous catalysts will no doubt be accelerated by the introduction of such combinatorial approaches.

A major difficulty with these processes is the lack of fast and reliable testing methods for rapid screening and optimization of the materials. Recently, a parallel screening method based on reaction heat formation has been reported (F. C. Moates et al., *Ind. Eng. Chem. Res.* 35, 4801–4803, 1996). For oxidation of hydrogen over a metallic surface, it is possible to obtain IR radiation images of an array of catalysts. The hot spots in the image correspond to active catalysts and can be resolved by an infrared camera.

Screening large arrays of materials in combinatorial libraries creates a number of challenges for existing analytical techniques. For example, traditionally, a heterogeneous catalyst is characterized by the use of a micro-reactor that contains a few grams of porous-supported catalysts. Unfortunately, the traditional method cannot be used to screen a catalyst library generated with combinatorial methods. First, a heterogeneous catalyst library synthesized by a combinatorial chemistry method may contain from a few hundred to many thousands of catalysts. It is impractical to synthesize a few grams of each catalyst in a combinatorial format. Second, the response time of micro-reactors is typically on the order of a few minutes. The time it takes to reach equilibrium conditions is even longer. It is difficult to achieve high-throughput screening with such long response times.

Another challenge with screening catalyst arrays is the low concentration of components that may be present in the reactions. For example, oxidation of ethylene to ethylene oxide can be carried out over a silver-based catalyst (S. Rebsdat et al., U.S. Pat. Nos. 4,471,071 and 4,808,738). For a surface-supported catalyst with an area of 1 mm by 1 mm and the same activity as the industrial catalyst, only about 10 parts per billion (ppb) of ethylene are converted into the desired ethylene oxide when the contact time is one second.

Detection of such low component levels in the presence of several atmospheres of reaction mixture is a challenge to analytical methods. Many analytical techniques, including optical methods such as four-wave mixing spectroscopy and cavity ring-down absorption spectroscopy as well as conventional methods such as GC/MS, are excluded because of poor sensitivities, non-universal detectability, and/or slow response. Therefore an apparatus and methodology for screening a substrate having an array of materials that differ slightly in chemical composition, concentration, stoichiometry, and/or thickness is desirable.

SUMMARY OF THE INVENTION

The present invention provides methods and apparatus for interrogating an array of diverse materials located at predefined regions on a single substrate. Typically, each of the individual materials will be screened or interrogated for one or more properties. Once screened, the individual materials may be ranked or otherwise compared relative to each other with respect to the material characteristics under investigation.

In one aspect of the invention, systems and methods are provided for imaging a library of materials using ultrasonic imaging techniques. The system includes one or more devices for exciting an element of the library such that acoustic waves are propagated through, and from, the element. The acoustic waves propagated from the element are detected and processed to yield a visual image of the library element. The acoustic wave data can also be processed to obtain information about the elastic properties of the library element. In one embodiment of the invention, the acoustic wave detector scans the library in a raster pattern, thus providing a visual image of the entire library.

In another aspect of the invention, systems and methods are provided for generating acoustic waves in a tank filled with a coupling liquid. The library of materials is then placed in the tank and the surface of the coupling liquid is scanned with a laser beam. The structure of the liquid surface disturbed by the acoustic wave is recorded, the recorded disturbance being representative of the physical structure of the library. Accordingly, a correspondence between the surface pattern and the geometry and mechanical properties of the library can be constructed.

In another aspect of the invention, a probe that includes a mechanical resonator is used to evaluate various properties (e.g., molecular weight, viscosity, specific weight, elasticity, dielectric constant, conductivity, etc.) of the individual liquid elements of a library of materials. The resonator is designed to ineffectively excite acoustic waves. The frequency response of the resonator is measured for the liquid element under test, preferably as a function of time. By calibrating the resonator to a set of standard liquids with known properties, the properties of the unknown liquid can be determined. An array of library elements can be characterized by a single scanning transducer or by using an array of transducers corresponding to the array of library elements.

A further understanding of the nature and advantages of the inventions herein may be realized by reference to the remaining portions of the specification and the attached drawings.

DETAILED DESCRIPTION OF THE INVENTION AND PREFERRED EMBODIMENTS

Glossary

Figure 1:
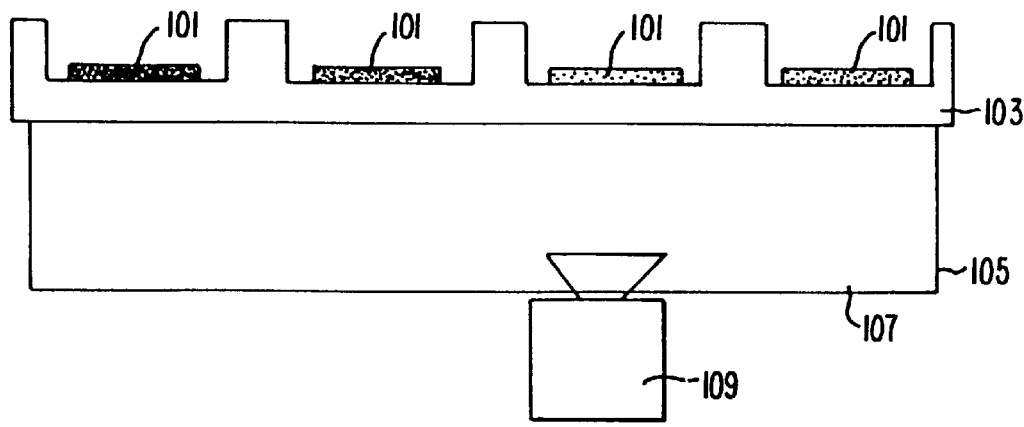
FIG. 1 is an illustration of a transducer-lens system for imaging a library of elements.

The following terms are intended to have the following general meanings as used herein.

Substrate:

A substrate is a material having a rigid or semi-rigid surface. In many embodiments at least one surface of the substrate will be substantially flat. In some embodiments the substrate will contain physical separations between synthesis regions for different materials. Suitable physical separations include, for example, dimples, wells, raised regions, and etched trenches. According to other embodiments, small beads or pellets may be provided on the surface, either alone or within substrate surface dimples. The surface area of the substrate is designed to meet the requirements of a particular application. Typically, the surface area of the substrate is in the range of 1 cm$^2$ to 400 cm$^2$. However, other sizes may be used with the present invention, for example surface areas as small as 0.001 cm$^2$ or as large as 10 m$^2$ are possible.

Predefined Region:

A predefined region is a localized area on a substrate that is, was, or is intended to be used for the formation of a specific material. The predefined region may be referred to, in the alternative, as a "known" region, a "reaction" region, a "selected" region, or simply a "region." The predefined region may have any convenient shape, e.g., linear, circular, rectangular, elliptical, or wedge-shaped. Additionally, the predefined region can be a bead or pellet which is coated with the component(s) of interest. In this embodiment, the bead or pellet can be identified with a tag, such as an etched binary bar code, that can be used to identify which components were deposited on the bead or pellet. The area of the predefined regions depends on the application and is typically smaller than about 25 cm$^2$. However, the predefined regions may be smaller than 10 cm$^2$, smaller than 5 cm$^2$, smaller than 1 cm$^2$, smaller than 1 mm$^2$, smaller than 0.5 mm$^2$, smaller than 10,000 $\mu$m$^2$, smaller than 1,000 $\mu$m$^2$, smaller than 100 $\mu$m$^2$, or even smaller than 10 $\mu$m$^2$.

Radiation:

Radiation refers to energy with a wavelength between $10^{-14}$ and $10^4$. Examples of such radiation include electron beam radiation, gamma radiation, x-ray radiation, ultraviolet radiation, visible light, infrared radiation, microwave radiation, and radio waves. Irradiation refers to the application of radiation to a surface or an object.

Component:

Component is used herein to refer to each of the individual substances that are deposited onto a substrate. Components can act upon one another to produce a particular material. Components can react directly with each other or with an external energy source such as radiation, an electric field, or a magnetic field. A third material or a chemical substance can also act upon components. A component can be an element, a chemical, a material, or a mixture of elements and chemicals. Components can form layers, blends or mixtures, or combinations thereof.

Source Material:

The term source material is used herein to refer to the original material from which a component was derived. Source materials can be composed of elements, compounds, chemicals, molecules, etc. that are dissolved in a solvent, vaporized, evaporated, boiled, sublimed, ablated, etc., thus allowing the source materials to deposit onto a substrate during the synthesis process.

Resulting Material:

The term resulting material is used herein to refer to the component or combination of components that have been deposited onto a predefined region of a substrate. The resulting materials may comprise a single component, or a combination of components that have reacted directly with each other or with an external source. Alternatively, the resulting material may comprise a layer, blend or mixture of components on a predefined region of the substrate. The resulting materials are screened for specific properties or characteristics to determine their relative performance.

Mixture or Blend:

The term mixture or, interchangeably, blend refers to a collection of molecules, ions, electrons, or chemical substances. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

Layer:

The term layer is used herein to refer to a material that separates one material, component, substrate or environment from another. A layer is often thin in relation to its area and covers the material beneath it. A layer may or may not be thin or flat, but once it is deposited it generally covers the entire surface such that it separates the component or substrate below the layer from the component or environment above the layer.

Heterogeneous Catalysts:

Heterogeneous catalysts enable catalytic reactions to occur with the reactants and catalysts residing in different phases. As used herein, heterogeneous catalysts include, but are not limited to, mixed metal oxides, mixed metal nitrides, mixed metal sulfides, mixed metal carbides, mixed metal fluorides, mixed metal silicates, mixed metal aluminates, mixed metal phosphates, nobel metals, zeolites, metal alloys, intermetallic compounds, inorganic mixtures, inorganic compounds, and inorganic salts.

Homogeneous Catalysts:

Homogeneous catalysts enable catalytic reactions to occur with the reactants and catalysts residing in the same phase. As used herein, homogeneous catalysts include, but are not limited to, catalysts for the polymerization of one or more olefinic or vinyl monomers. The olefinic monomers include, but are not limited to, ethylene or alpha-olefins containing from 3 to 10 carbon atoms, such as propylene, 1-butene, 1-pentane, 1-hexene, and 1-octene. The vinyl monomers include, but are not limited to, vinyl chloride, vinyl acetate, vinyl acrylate, methylmethacrylate, methyl vinyl ether, ethyl vinyl ether and acetonitrile. The catalysts employed to carry out a polymerization of one or more monomers of this type include, but are not limited to, radical catalysts, cationic catalysts, anionic catalysts, and anionic coordination catalysts.

Generating Arrays of Materials

Generally, an array of materials is prepared by successively delivering components of the materials to predefined regions on a substrate, and simultaneously reacting the components to form at least two materials or, alternatively, the components are allowed to interact to form at least two materials. In one embodiment, for example, a first component of a first material is delivered to a first predefined location on a substrate, and a first component of a second material is delivered to a second predefined region on the same substrate. Simultaneously with or thereafter, a second component of the first material is delivered to the first region on the substrate, and a second component of the second material is delivered to the second region on the substrate. Each component can be delivered in either a uniform or gradient fashion to produce either a single stoichiometry or, alternatively, a large number of stoichiometries within a single predefined region. The process is repeated, with additional components, to form a vast array of components at predefined locations on the substrate. Thereafter, the components are simultaneously reacted to form at least two materials or, alternatively, the components interact to form at least two materials. As described herein, the components can be sequentially or simultaneously delivered to the predefined regions on the substrate using any of a number of different delivery techniques.

Numerous combinatorial techniques can be used to synthesize the various arrays of diverse materials on the substrate according to the present invention. For example, in one embodiment a first component of a first and second material is delivered to the predefined regions on the substrate. Then a second component of the first and second materials is delivered to the predefined regions on the substrate. This process continues for the other components (e.g., third, fourth, fifth, etc. components) and/or the other materials (e.g., third, fourth, fifth, etc. materials) until the array is complete. In another embodiment, the array is formed as previously described, but the resulting materials are formed immediately as the components contact each other on the substrate. In yet another embodiment, the array is formed as previously described, but after the various components are delivered to the substrate, a processing step is carried out which allows or causes the components to interact. In still another embodiment, two or more components are delivered to the predefined regions on the substrate using fast sequential or parallel delivery techniques such that the components interact with each other before contacting the substrate.

Essentially, any conceivable substrate can be employed in the invention. The substrate can be organic, inorganic, biological, nonbiological, or a combination thereof. The substrate can exist in a variety of forms utilizing any convenient shape or configuration. The substrate preferably contains an array of depressions or wells in which the synthesis of the library takes place. The substrate preferably forms a rigid support on which to carry out the reactions described herein. The substrate may be any of a wide variety of materials including, for example, polymers, plastics, pyrex, quartz, resins, silicon, silica or silica-based materials, carbon, metals, inorganic glasses, inorganic crystals, and membranes. Upon review of this disclosure, other substrate materials will be readily apparent to those of skill in the art. Surfaces on the solid substrate can be composed of the same materials as the substrate or, alternatively, they can be different (i.e., the substrates can be coated with a different material). Moreover, the substrate surface can contain thereon an adsorbent (for example, cellulose) to which the components of interest are delivered. The most appropriate substrate and substrate-surface materials will depend on the class of materials to be synthesized and the selection in any given case will be readily apparent to those of skill in the art.

Generally, physical masking systems can be employed in combination with various deposition techniques in order to apply components onto the substrate, preferably in an array of wells, in a combinatorial fashion. Thus arrays of resulting materials are created within predefined locations or wells on the substrate. The arrays of resulting materials will usually differ in composition and stoichiometry. Although the components are typically dispensed in the form of a liquid, one or more components may be dispensed in the form of a gas or a powder. Therefore primarily solution phase deposition techniques are used including, for example, sougel methods, discrete liquid dispensing techniques (e.g. pipettes, syringes, ink jets, etc.), spin coating with lithography, microcontact printing, spraying with masks and immersion impregnation. Other techniques may be used, however, such as sputtering, electron-beam and thermal evaporation, laser deposition, ion beam deposition, chemical vapor deposition, and spray-coating, Dispenser systems can be manual or, alternatively, they can be automated using, for example, robotics techniques. A description of systems and methods for generating arrays of materials can be found in commonly assigned, co-pending patent applications "The Combinatorial Synthesis Of Novel Materials", Publication No. WO 95/13278, filed Oct. 18, 1995; "Systems and Methods for the Combinatorial Synthesis of Novel Materials," patent application Ser. No. 08/841,423, filed Apr. 22, 1997; and "Discovery of Phosphor Materials Using Combinatorial Synthesis Techniques," provisional patent application Serial No. 60/039,882, filed Mar. 4, 1997; the complete disclosures of which are incorporated herein by reference for all purposes.

In some embodiments of the present invention, after the components have been deposited onto or within predefined regions on a substrate, they are reacted using a number of different techniques. For example, the components can be reacted using solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent, etc. Furthermore, each predefined region on the substrate can be heated simultaneously or sequentially using heat sources such as focussed infrared radiation, resistive heating, etc. Reactants can, for example, be dispensed to the library of elements in the form of a gas or a liquid. Other useful techniques that can be used to react the components of interest will be readily apparent to those of skill in the art. Additionally, components can react with each other instantly, upon contacting each other, or in the air before contacting the substrate.

Once prepared, the array of resulting materials can be screened for useful properties and/or the resulting materials can be ranked, or otherwise compared, using the methods described herein. Either the entire array or, alternatively, a section thereof (e.g., a row of predefined regions) can be screened using parallel or fast sequential screening. The area and/or volume of the predefined regions varies, as does the number and density of regions per substrate, depending upon the specific intended application. Similarly, the number of different materials contained within an array also varies with the intended application. Resulting materials include, but are not limited to, liquids, dissolved organic or inorganic molecules, non-biological organic polymers, polymers partially or fully dissolved in a solvent, covalent network solids, ionic solids and molecular, inorganic materials, intermetallic materials, metal alloys, ceramic materials, organic material, organometallic materials, composite materials (e.g., inorganic composites, organic composites, or combinations thereof), and homogeneous or heterogeneous catalysts.

Given the chemical complexity of catalytic systems, the lack of predictive models, the number of possible combinations of metals, counterions, ligands, and supports, and the time consuming process of evaluating the performance of each catalyst formulation utilizing conventional laboratory pilot reactors, it is not surprising that the search for the optimum catalyst is a time consuming and inefficient process. Thus, a combinatorial approach to the discovery and optimization of catalytic systems, which combines the synthesis of catalyst libraries with the screening tools of this invention, is useful for accelerating the pace of research in this field. The catalyst libraries of the present invention can include organic (e.g., catalytic antibodies), organometallic, heterogeneous or solid state inorganic array elements. For purposes of this invention, a catalyst is defined as any material that accelerates the rate of a chemical reaction and which is either not consumed during the reaction or which is consumed at a rate slower (on a molar basis) than the reaction that is being catalyzed. Organometallic catalyst libraries which can be screened for useful catalytic properties include, but are not limited to, those described in co-pending U.S. patent application Ser. No. 08/898,715, filed Jul. 22, 1997, which is hereby incorporated by reference for all purposes.

Ultrasonic Imaging

In this aspect of the invention, systems and methods are provided for imaging libraries of materials with ultrasonic imaging techniques. In a first embodiment, an acoustic apparatus and method for imaging of a library of materials is provided. The apparatus includes a device for generating acoustic waves that can propagate into a member or element of interest within a library and a detector for sensing the propagation and reflection of the acoustic waves from the library elements. The source and the detector of acoustic waves may be the same apparatus, typically a piezoelectric crystal. After detecting the acoustic waves propagated from the element, the library and the acoustic wave detector are moved relative to one another, preferably in a raster scanning pattern. The magnitude and phase of the detected acoustic waves and the corresponding scan pattern of the library are recorded so that visual images of the library can be obtained. In addition, by processing the obtained data in accordance with a model of sample-acoustic beam interaction, information about the elastic properties of individual library members can be calculated. From the relative elastic properties of elements in the library, relative measures of such properties as molecular weight, branching, and co-monomer content may be inferred.

In a second embodiment of the invention, acoustic waves are generated in a tank filled with a coupling liquid using a conventional multi-element ultrasound imaging head or one of custom design. The library of elements is placed within the tank such that acoustic waves move from the transducer through the fluid, across the substrate, and into the elements of the library. The reflections from each interface and from within the individual library elements are recorded by the ultrasound transducer head. Material properties can be calculated from the recorded temporal pattern. Alternatively, the structure or morphology of the surface of the library elements, or a liquid interface deposited on top of them, may be recorded using a laser probe or other imaging system. Furthermore, since the recorded disturbance is representative of the physical structure of the library, a correspondence between the surface pattern and the geometry and mechanical properties of the library can be constructed. Lastly, the collected data can be used to derive microscopic properties of individual elements of the library, for example, sound velocity and attenuation as a function of element position can be derived.

In a third embodiment of the invention, an acoustic lens excites acoustic waves within elements of the material array. The excited acoustic waves are in a form of short pulses. The magnitude of the echoes produced by the acoustic waves is measured, as is the time delay between the excitation pulses and the echoes from the liquid-material and material-substrate interfaces. The library and the acoustic wave detector are moved relative to one another in a raster scanning pattern and the collected data is recorded. Based upon the collected data an acoustic image of the library can be generated. The time-resolved image can give valuable information about library topography. For example, the first echo provides information related to the impedance mismatching on the element-coupling liquid interface and the second echo provides information about the sound velocity distribution in the element material.

In a fourth embodiment of the invention, individual piezoelectric transducers are integrated into the substrate. Typically the transducers are fabricated into the substrate using standard fabrication techniques. The library elements are then deposited onto the substrate such that each individual library element corresponds to an individual piezoelectric transducer. The transducers serve the dual function of exciting the acoustic wave and receiving the return wave.

FIG. 1 is an illustration of a transducer-lens system coupled to a library. The library is comprised of an array of elements 101 contained within or on a substrate 103. Substrate 103 is coupled to a tank 105 containing a coupling medium 107. Coupling medium 107, selected on the basis of its acoustic properties, is selected from a variety of liquids, for example, water, mercury, etc. A transducer-lens system 109 provides the acoustic waves that pass through liquid 107 and are coupled into elements 101 and substrate 103. Transducer-lens system 109 is also used to measure the magnitude and time delay between the excitation pulses and the echoes. If desired, the excitation transducer may be separate from the receiving transducer. As described above, transducer-lens 109 is scanned across the array in order to obtain information about the entire array. Alternatively, an array of transducer-lenses may be used (not shown) as is used in conventional ultrasound imaging.

Figure 2:
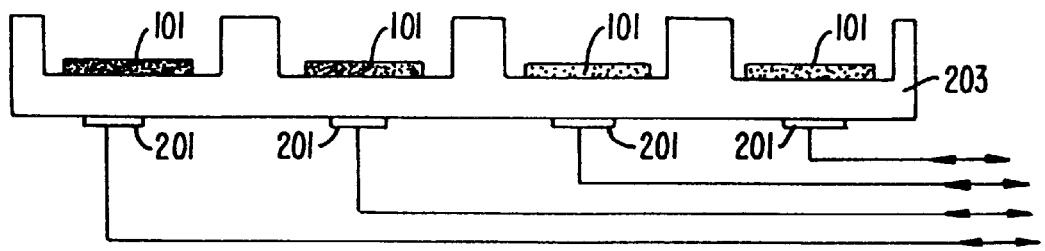
FIG. 2 illustrates an ultrasonic imaging system utilizing a piezoelectric transducer array.

FIG. 2 illustrates a combinatorial library synthesized on a substrate consisting of integrated piezoelectric transducers. In the preferred embodiment, the individual piezoelectric transducers 201 comprising the transducer array are directly incorporated into substrate 103. Each transducer 201 is aligned such that it is directly adjacent to a corresponding library element 101. Transducers 201 serve as both the transmitters and receivers of the acoustic energy. The output signals from transducers 201 can be multiplexed for serial readout. In an alternative embodiment, transducers 201 are mounted onto a separate substrate (not shown) that is brought into contact with substrate 103. In another alternative embodiment, substrate 103 is formed of a piezoelectric material and electrodes are attached directly under each library element (not shown).

Mechanical Oscillator Probes

Although ultrasonic transducers can be used to determine a variety of material properties, this technique is not suitable for all liquids. Typically the size of the transducer and the cell should be much greater than the acoustic wavelength, otherwise the diffraction effects and steady waves within the cell become too complicated. For a cell on the order of a few centimeters, the frequency should be above 1 MHz. However complex liquids and solutions, such as polymer solutions, often behave like elastic gels at high frequencies due to their relaxation time corresponding to significantly lower frequencies.

Shear-mode transducers as well as various surface-wave transducers can be used to avoid some of the problems associated with typical ultrasonic transducers. Since leaky surface acoustic waves decay exponentially with the distance from the sensor surface, such sensors tend to be insensitive to the geometry of the measurement volume, thus eliminating most diffraction and reflection problems. Furthermore, such sensors are cheap, reproducible, and can be used to construct high throughput screening devices. Unfortunately the operation frequency of these sensors is also high, thus restricting their applicability as mentioned above. Moreover, at such frequencies only a very thin layer of liquid near the sensor surface will influence the response of the sensor. Thus modification of the surface of the sensor through adsorption of solution components will often result in dramatic changes in properties associated with the sensor.

Figure 3:
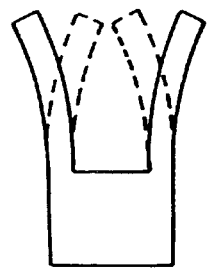
FIG. 3 illustrates the oscillation mode of a tuning fork resonator.
Figure 4:
FIG. 4 illustrates the oscillation mode of a bimorph/unimorph resonator.

To eliminate the effects of diffraction, acoustic wave interference, and measurement cell geometry, it is preferable to use a transducer or sensor that does not excite acoustic waves. A sensor that is much smaller than the wavelength accomplishes these goals, providing an oscillator that ineffectively excites acoustic waves in the surrounding media. Designing the different parts of the sensor to oscillate in opposite phases can enhance this effect. In such a resonator most of the mechanical energy associated with the oscillation dissipates due to the viscosity, both shear and bulk, of the liquid involved in the oscillatory motion. The sensor produces a hydrodynamic flow velocity field that decays with the distance from sensor. Thus liquid at a distance a few times greater than the sensor dimension remains practically unperturbed. If the measurement cell is large enough to contain the field of perturbation, the device becomes insensitive to the cell geometry. Examples of suitable oscillators include piezoceramic and quartz resonators embodied in the form of a tuning fork, a unimorph, or a bimorph. FIGS. 3 and 4 illustrate the oscillation modes of tuning fork and bimorph/unimorph resonators, respectively.

Typically a system according to the invention uses an AC voltage source to excite oscillation of the resonator. The system also includes a receiver which measures the frequency response of the resonator in the liquid under test. The response of the resonator varies depending upon the viscosity, specific weight, and elasticity of the liquid under test. In some cases the dielectric constant and the conductivity of the liquid can influence the response of the resonator. If properties of the liquid vary with time, the response of the resonator will similarly vary. By calibrating the resonator to a set of standard liquids with known properties, the properties of an unknown liquid can be determined from the response of the resonator.

Figure 5:
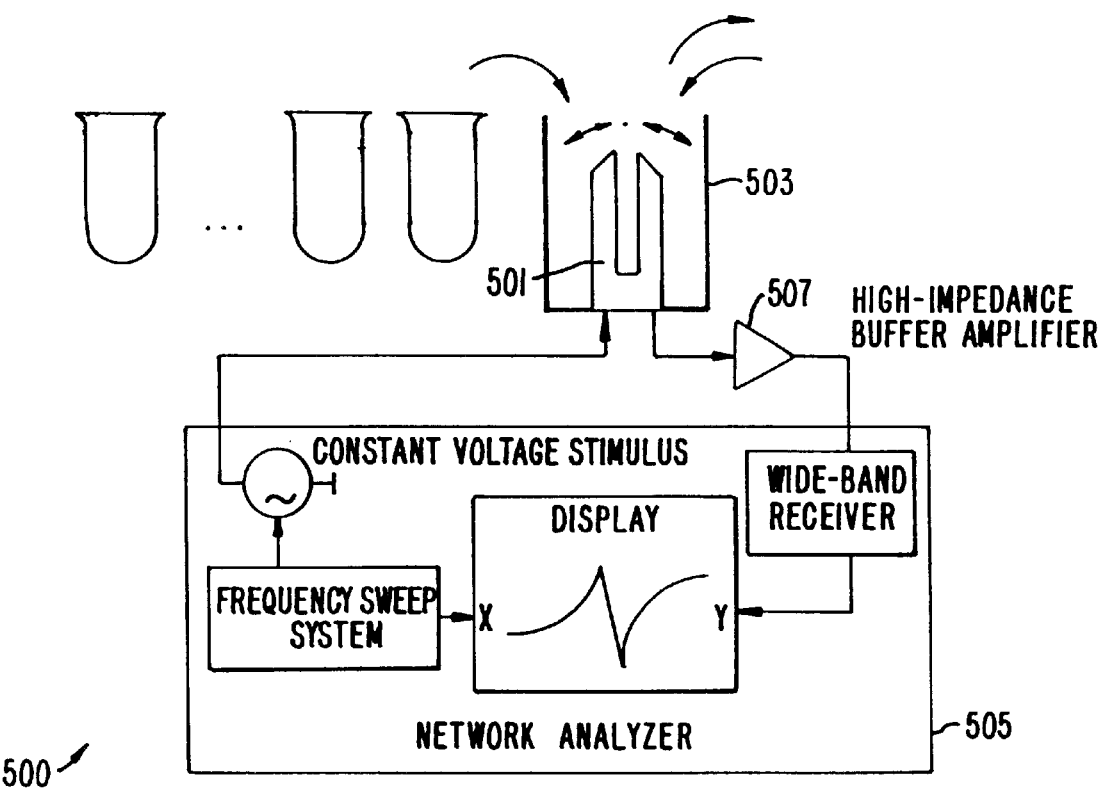
FIG. 5 illustrates an embodiment of the invention used to determine the average molecular weight of polystyrene in toluene during polymerization.

In one embodiment of the invention illustrated in FIG. 5, a tuning fork resonator system 500 is used to monitor the average molecular weight of polystyrene in toluene solutions during polymerization reactions. This configuration is not limited to this polymerization reaction, rather, the polymerization reaction is simply used as an example of an application of this embodiment. The monitoring of the forming polymer's properties in the presence of a polymerization catalyst and possibly a solvent is essential in order to estimate catalytic activity and conversion rate.

In use, a tuning fork resonator 501 is placed within a well 503 containing the liquid to be tested. Preferably well 503 is one well of a plurality of wells contained within an array. Resonator 501 is typically coupled to a probe and the probe is scanned from sample well to sample well in a raster fashion. Alternatively, an array of resonator probes can be fabricated corresponding to the array of wells or some subset thereof, thus allowing a large number of wells to be simultaneously tested. In the embodiment illustrated in FIG. 5, a network analyzer 505, such as a HP8751A Analyzer, is used to excite the resonator oscillations and to receive the response of the oscillator at various frequencies. Resonator response is then recorded as a function of excitation frequency. The output signal of resonator 501 passes through a high impedance buffer amplifier 507 prior to being measured by the analyzer's wide band receiver 509.

Figure 6:
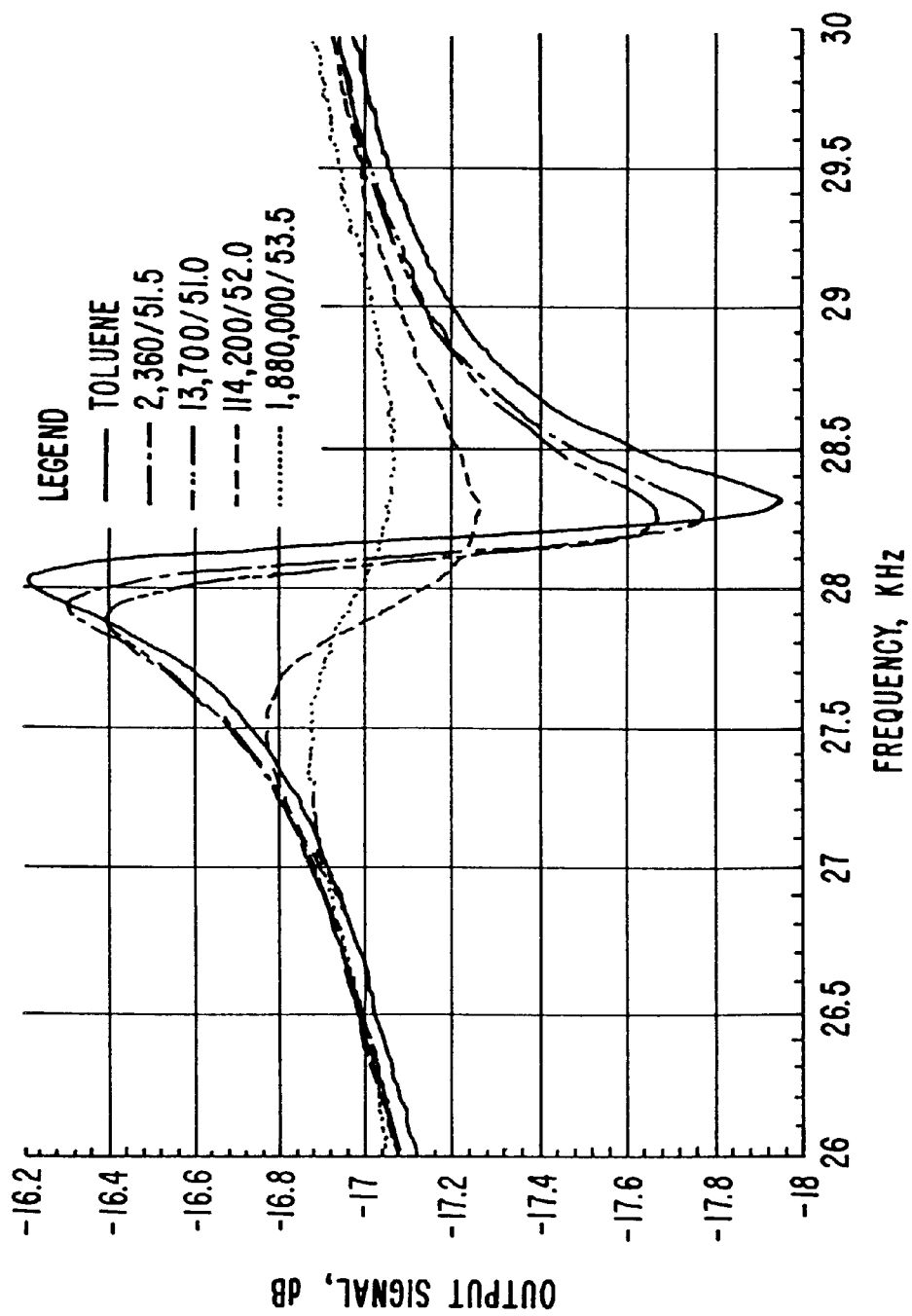
FIG. 6 is a graph of the frequency response of a tuning fork resonator for pure toluene and four different molecular weights of polystyrene.

System 500 was calibrated using a set of standard solutions of polystyrene at a constant concentration of 52 mg/ml. In pure toluene, the frequency of the resonator fundamental mode was 28 kHz. FIG. 6 is a graph of the frequency responses of resonator 501 for pure toluene and four different molecular weights of polystyrene. The distance between the frequency response curve for toluene and an i-polymer solution was calibrated using the set of different molecular weights. This distance is given by:

$$d_i = \left( \frac{1}{f_1 - f_0} \int_{f_0}^{f_1} (R_0 - R_i)^2 \, df \right)^{\frac{1}{2}}$$

where $f_0$ and $f_1$ are the start and stop frequencies, respectively, $R_0$ is the frequency response of the resonator in toluene, and $R_i$ is the resonator response in the i-polymer solution.

Figure 7:
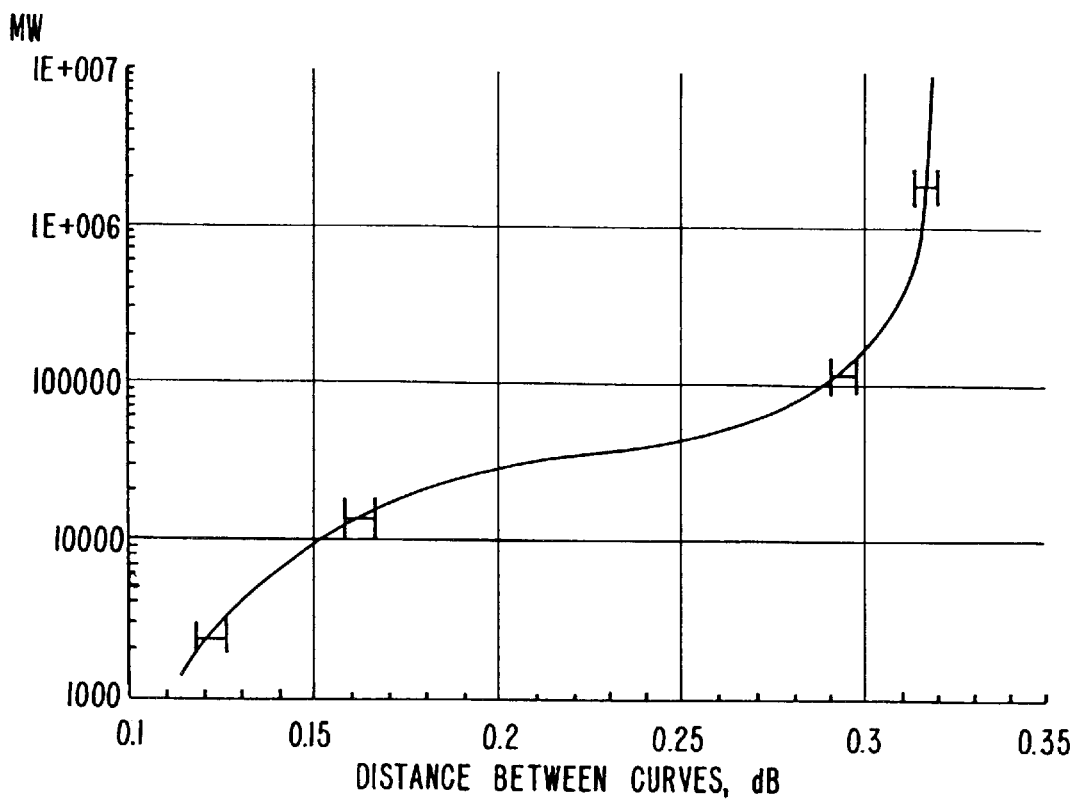
FIG. 7 is a graph of a calibration curve corresponding to the data shown in FIG. 6.

FIG. 7 is a graph of a calibration curve corresponding to this data. The test points and associated error bars are indicated on this curve. Obviously additional calibration curves can be taken as necessary. The graph of FIG. 7 shows that for this particular resonator design, the best accuracy is achieved for molecular weights in the range of 10,000 to 100,000.

To monitor a polymerization reaction, resonator probe 501 is placed in a measurement well 503 filled with pure toluene and the catalyst. The frequency response of the sensor for this solution is recorded. Resonator probe 501 is then placed in a measurement well 503 filled with toluene in which a low molecular weight polystyrene has been dissolved. After the catalyst is added, the frequency response of the resonator is recorded at intervals, typically between 10 and 30 seconds. The distance of the response curve for the polymer from that of pure toluene is then calculated in accordance with the formula given above. The molecular weight of the polymer is calculated using the calibration curve of FIG. 7.

As discussed above, depending upon the liquid to be tested, other resonator designs may be used. For example, to improve the suppression of acoustic waves, a tuning fork resonator with four tines can be used. It is also possible to excite resonator oscillations through the use of voltage spikes instead of a frequency sweeping AC source. In this case the decaying free oscillations of the resonator are recorded instead of the frequency response. A variety of signal processing techniques well known by those of skill in the art can be used.

Figure 8:
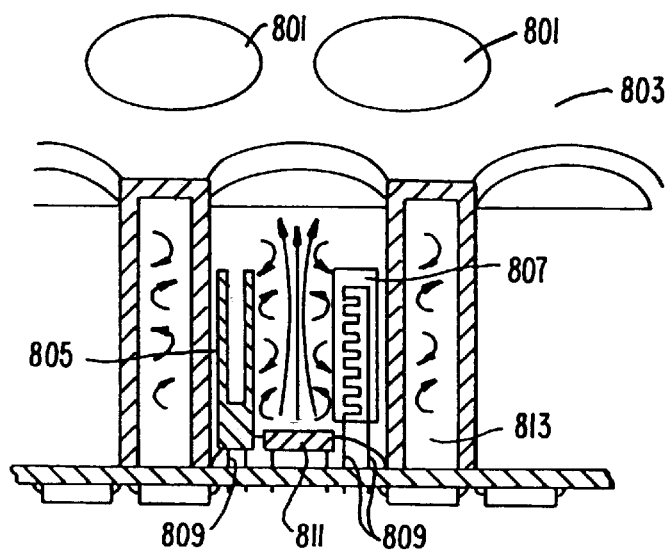
FIG. 8 illustrates an embodiment of the invention used for high throughput screening of catalyst combinatorial libraries.

FIG. 8 illustrates an embodiment of the invention that can be used for high throughput screening of catalyst combinatorial libraries. The embodiment monitors the molecular weight and concentration, if necessary, of a polymer in a solution in the presence of different catalysts while the reactions are running. Preferably the system also includes means for monitoring the heat generated during the reactions. Thus hundreds of catalysts can be evaluated in a single experiment for such characteristics as selectivity, conversion rate, etc.

An array of measurement wells 801 is contained within a substrate 803. Within each well 801 is a resonator 805 for molecular weight determination and a thermistor 807 for heat of reaction determination. Preferably contacts 809 for resonator 805 and thermistor 807 pass through the bottom of substrate 803 where they are connected to the necessary electronics. Much of the electronics can be mounted directly to the bottom of substrate 803, simplifying the overall system design. However, as previously described, the array of resonator probes can also be fabricated as a stand alone array to be placed within the corresponding measurement wells of a combinatorial library array during testing.

The measurement package within each well 801 may also contain an agitator 811 to insure uniform concentration distribution within the well. Typically agitator 811 is not required if well 801 is small enough to promote rapid concentration leveling due to diffusion. Besides monitoring the heat generated during the reactions, thermistors 807 may also be used to preheat the media within wells 801 up to a predefined temperature and to keep the temperature at the same level during the reactions. In a specific embodiment, a thermostatically controlled cooling liquid 813 passes between the walls of wells 801, thus providing a steady heat transfer from wells 801.

Figure 9:
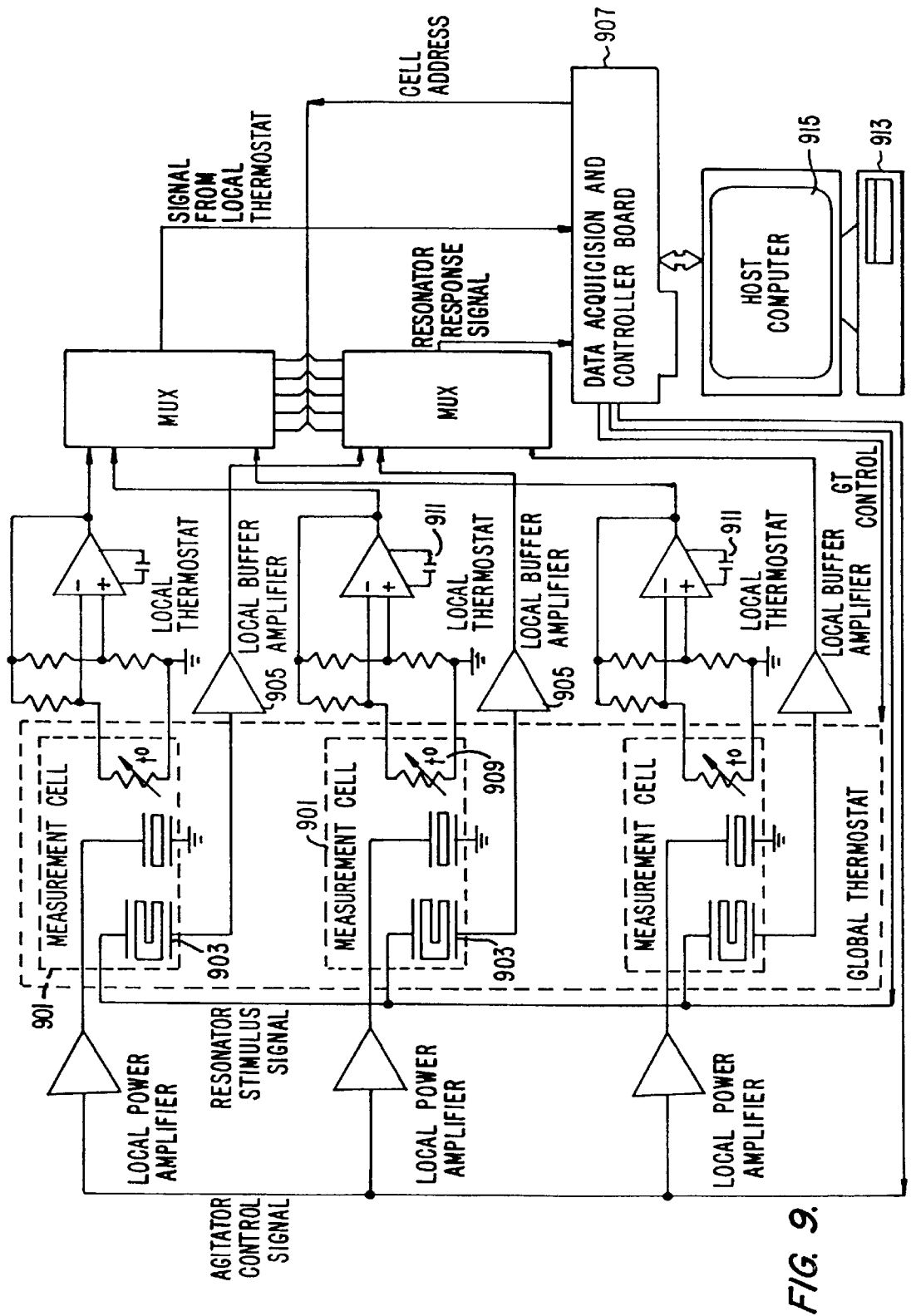
FIG. 9 is a simplified circuit diagram for a multiplexed control circuit suitable for use with the embodiment shown in FIG. 8.

FIG. 9 is a simplified circuit diagram for a multiplexed control circuit suitable for use with the embodiment shown in FIG. 8. Although only three measurement cells 901 are shown, this control circuit can be used to multiplex a large array of cells. The output of a resonator 903 passes through a local buffer amplifier 905 before being multiplexed into a data acquisition system 907. Coupled to each thermistor 909 is a thermostat 911. The heat produced by a reaction causes local thermostat 911 to drop down the voltage across thermistor 909 to keep its temperature at the same level. As with the resonator output, this voltage is multiplexed and acquired by data acquisition system 907. Thus the heat production given by each reaction can be easily calculated at any time, providing information about the activity of a particular catalyst. The data acquired by system 907 is processed by processor 913 and presented to the user via monitor 915. The data may also be stored in memory resident within processor 913. From this data the reactions occurring in the various wells may be simultaneously characterized.

In an alternate embodiment, multiple resonators are used within each single well of an array. The multiple resonators typically have a different resonance frequency and/or geometry. This embodiment offers several advantages to the previous embodiment utilizing a single resonator per well. First, the dynamic sensing range of the system may be greatly extended since each of the individual resonators may be designed to cover a different frequency range. Second, the sensitivity over the sensing range may be enhanced since each resonator may be designed to be sensitive to a different frequency range. For example, the graph illustrated in FIG. 7 shows that for this particular resonator design, the best accuracy was achieved for molecular weights in the range of 10,000 to 100,000. Utilizing the present embodiment, a resonator with the accuracy shown above could be combined in a single sample well with a resonator having improved accuracy in the 100,000 to 1,000,000 range, thus providing superlative sensing capabilities throughout the 10,000 to 1,000,000 range for a single sample well. The signals from the independent resonators may be analyzed using such methods as neural networks, etc.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method of screening an array of liquid materials for a selected property, the method comprising:

providing an array of liquid materials;

contacting the array of liquid materials with low frequency unimorph resonators, the resonators designed to minimize excitation of acoustic waves and calibrated against a set of standard liquids to yield calibrations relating the selected property of responses of the resonators to a stimulus;

applying a stimulus to the resonators causing the resonators to oscillate;

periodically monitoring responses of the resonator to the stimulus;

monitoring heat generated or consumed by the array of liquid materials; and measuring the selected property of the array of liquid materials based on the monitored responses and calibrations.

2. The method of claim 1, wherein the selected property is selected from the group consisting of molecular weight, viscosity, specific weight, elasticity, dielectric constant, and conductivity.

3. The method of claim 1, wherein the stimulus is an excitation frequency varying in a predefined manner.

4. The method of claim 1, wherein the responses of the resonators to the stimulus are monitored as functions of time.

5. The method of claim 1, wherein the array of liquid materials is a combinatorial array.

6. The method of claim 1, further comprising agitating the array of liquid materials during monitoring.

7. The method of claim 6, wherein agitation is performed by an array of individual agitators.

8. The method of claim 1, wherein the stimulus is a voltage spike.

9. The method of claim 1, wherein the array of liquid materials comprises an array of gels.

10. The method of claim 1, further comprising:

contacting at least one sample of the array of liquid materials with at least two of the low frequency resonators.

11. The method of claim 1, wherein at least one sample of the array of liquid materials includes a catalyst.

12. A system for determining a selected property of an array of liquid materials, the system comprising:

an array of sample wells for containing the array of liquid materials, wherein the array of sample wells is a microtitrate plate;

low frequency unimorph resonators disposed in the array of sample wells, the low frequency resonators designed to minimize excitation of acoustic waves and calibrated against a set of standard liquids to yield calibrations relating the selected property to responses of the resonators to an oscillation stimulus;

a stimulus source coupled to the resonators for exciting oscillation of the resonators;

a receiver coupled to the resonators for periodically monitoring responses of the resonators to the stimulus; and a processor coupled to the stimulus source and the receiver, the processor activating the stimulus source for the resonators at predefined times and calculating the selected property of the array of liquid materials based on the frequency response and calibrations.

13. The system of claim 12, the array of liquid materials comprising an array of gels.

14. The system of claim 12, wherein at least two low frequency resonators are disposed within each of the sample wells.

15. The system of claim 12, wherein the selected property is selected from the group consisting of molecular weight, viscosity, specific weight, elasticity, dielectric constant and conductivity.

16. The system of claim 12 wherein the stimulus source applies an excitation frequency varying in a predefined manner to the resonators.

17. The system of claim 12, wherein the receiver is adapted to periodically monitor responses of the resonators to the stimulus as functions of time.

18. The system of claim 12, further comprising at least one catalyst in each of the sample wells.

19. The system of claim 18, wherein the array of liquid materials is a combinatorial array.

20. The system of claim 12, further comprising an agitator within each of the sample wells, the agitators providing substantially uniform concentration distribution within each of the sample wells.

21. The system of claim 12, wherein the stimulus source applies a voltage spike to the resonators.

22. A system for determining a selected property of an array of liquid materials, the system comprising:

an array of sample wells for containing the array of liquid materials;

low frequency unimorph resonators disposed in the array of sample wells, the low frequency resonators designed to minimize excitation of acoustic waves and calibrated against a set of standard liquids to yield calibrations relating the selected property to responses of the resonators to an oscillation stimulus;

a stimulus source coupled to the resonators for exciting oscillation of the resonators;

a receiver coupled to the resonators for periodically monitoring responses of the resonators to the stimulus;

a processor coupled to the stimulus source and the receiver, the processor activating the stimulus source for the resonators at predefined times and calculating the selected property of the array of liquid materials based on the frequency response and calibrations; and an array of heat regulators corresponding to the array of sample wells, wherein the array of heat regulators is coupled to the receiver, the receiver periodically monitoring an amount of energy required to maintain constant temperature, and wherein the processor calculates an amount of heat produced as a function of time within each of the sample wells from the monitored amount of required energy.

23. The system of claim 22, wherein the array of heat regulators maintains a constant temperature within the array of sample wells.

24. The system of claim 22, the array of heat regulators comprising an array of thermistors.

25. A method of screening an array of liquid materials for a selected property, the method comprising:

providing an array of liquid materials, at least one sample of the array of liquid materials containing a catalyst;

contacting the array of liquid materials with low frequency resonators, the resonators designed to minimize excitation of acoustic waves and calibrated against a set of standard liquids to yield calibrations relating the selected property to responses of the resonators to a stimulus;

applying a stimulus to the resonators causing the resonators to oscillate;

periodically monitoring responses of the resonators to the stimulus; and measuring the selected property of the array of liquid materials based on the monitored responses and calibrations.

26. The method of claim 25, wherein the responses of the resonators to the stimulus are monitored as functions of time.

27. The method of claim 25, wherein at least one of the resonators is a unimorph resonator.

28. A method of screening an array of liquid materials for a selected property, the method comprising:

providing an array of liquid materials;

contacting the array of liquid materials with low frequency resonators, the resonators designed to minimize excitation of acoustic waves and calibrated against a set of standard liquids to yield calibrations relating the selected property to responses of the resonators to a stimulus;

monitoring heat generated or consumed by the array of liquid materials;

applying a stimulus to the resonators causing the resonators to oscillate;

periodically monitoring responses of the resonators to the stimulus; and measuring the selected property of the array of liquid materials based on the monitored responses and calibrations.

29. The method of claim 28, wherein the responses of the resonators to the stimulus are monitored as functions of time.

30. The method of claim 28, wherein at least one of the resonators is a unimorph resonator.

31. A system for determining a selected property of an array of liquid materials, the system comprising:

a microtiter plate having wells for containing the array of liquid materials;

low frequency resonators at least partially disposed in the wells of the microtiter plate, the low frequency resonators designed to minimize excitation of acoustic waves and calibrated against a set of standard liquids to yield calibrations relating the selected property to responses of the resonators to a stimulus;

a stimulus source coupled to the resonators for exciting oscillation of the resonators;

a receiver coupled to the resonators for periodically monitoring responses of the resonators to the stimulus; and a processor coupled to the stimulus source and the receiver, the processor activating the stimulus source for the resonators at predefined times and calculating the selected property of the array of liquid materials based on the responses and calibrations.

32. The system of claim 31, wherein the receiver is adapted to periodically monitor responses of the resonators to the stimulus as functions of time.

33. The system of claim 31, wherein at least one of the resonators is a unimorph resonator.

34. A system for determining a selected property of an array of liquid materials, the system comprising:
   vessels for containing the array of liquid materials;
   low frequency resonators at least partially disposed in the vessels, the low frequency resonators designed to minimize excitation of acoustic waves and calibrated against a set of standard liquids to yield calibrations relating the selected property to responses of the resonators to a stimulus;
   a catalyst in at least one of the vessels;
   a stimulus source coupled to the resonators for exciting oscillation of the resonators;
   a receiver coupled to the resonators for periodically monitoring responses of the resonators to the stimulus; and
   a processor coupled to the stimulus source and the receiver, the processor activating the stimulus source for the resonators at predefined times and calculating the selected property of the array of liquid materials based on the responses and calibrations.

35. The system of claim 34, wherein the receiver is adapted to periodically monitor responses of the resonators to the stimulus as functions of time.

36. The system of claim 34, wherein at least one of the resonators is a unimorph resonator.

37. A system for determining a selected property of an array of liquid materials, the system comprising:
   vessels for containing the array of liquid materials;
   low frequency resonators at least partially disposed in the vessels, the low frequency resonators designed to minimize excitation of acoustic waves and calibrated against a set of standard liquids to yield calibrations relating the selected property to responses of the resonators to a stimulus;
   a stimulus source coupled to the resonators for exciting oscillation of the resonators;
   a receiver coupled to the resonators for periodically monitoring responses of the resonators to the stimulus;
   a processor coupled to the stimulus source and the receiver, the processor activating the stimulus source for the resonators at predefined times and calculating the selected property of the array of liquid materials based on the responses and calibrations; and
   heat regulators coupled to the vessels for monitoring heat generated or consumed by the array of liquid materials.

38. The system of claim 37, wherein the receiver is adapted to periodically monitor responses of the resonators to the stimulus as functions of time.

39. The system of claim 37, wherein at least one of the resonators is a unimorph resonator.

40. A method of screening an array of liquid materials for a selected property, the method comprising:
   providing an array of liquid materials;
   contacting the array of liquid materials with low frequency tuning fork resonators, the resonators designed to minimize excitation of acoustic waves and calibrated against a set of standard liquids to yield calibrations relating the selected property to responses of the resonators to a stimulus;
   applying a stimulus to the resonators causing the resonators to oscillate;
   periodically monitoring responses of the resonators to the stimulus; and
   measuring the selected property of the array of liquid materials based on the monitored responses and calibrations.

41. The method of claim 40, wherein the responses of the resonators to the stimulus are monitored as functions of time.

42. A method of screening an array of liquid materials for a selected property, the method comprising:
   providing an array of diverse liquid materials supported simultaneously by a common substrate;
   contacting the array of liquid materials with low frequency unimorph resonators, the resonators designed to minimize excitation of acoustic waves and calibrated against a set of standard liquids to yield calibrations relating the selected property of responses of the resonators to a stimulus;
   applying a stimulus to the resonators causing the resonators to oscillate;
   periodically monitoring responses of the resonator to the stimulus;
   screening the array of liquid materials for the selected property based on the monitored responses and calibrations; and
   comparing the selected property with respect to members of the array of materials.

43. The method of claim 42, wherein comparing the data of the screening includes ranking the members of the array of materials with respect to each other.

44. The method of claim 42, wherein the selected property is selected from the group consisting of molecular weight, viscosity, specific weight, elasticity, dielectric constant, and conductivity.

45. The method of claim 42, wherein the stimulus is an excitation frequency varying in a predefined manner.

46. The method of claim 42, wherein the responses of the resonators to the stimulus are monitored as functions of time.

47. The method of claim 42, wherein the array of liquid materials is a combinatorial array.

48. The method of claim 42, further comprising monitoring heat generated or consumed by the array of liquid materials.

49. The method of claim 42, further comprising agitating the array of liquid materials during monitoring.

50. The method of claim 49, wherein agitation is performed by an array of individual agitators.

51. The method of claim 42, wherein the stimulus is a voltage spike.

52. The method of claim 42, wherein the array of liquid materials comprises an array of gels.

53. The method of claim 42, further comprising:
   contacting at least one sample of the array of liquid materials with at least two of the low frequency resonators.

54. The method of claim 42, wherein at least one sample of the array of liquid materials includes a catalyst.

* * * * *